United States Patent [19]

Schmieder et al.

[11] 4,212,723

[45] Jul. 15, 1980

[54] COUNTERFLOW EXTRACTION COLUMN

[75] Inventors: Helmut Schmieder, Karlsruhe; Hubert Goldacker, Linkenheim; Ernst Warnecke, Ladenburg; Manfred Kluth, Neuthard; Reinhard Schlenker, Eggenstein, all of Fed. Rep. of Germany

[73] Assignee: Kernforschungszentrum Karlsruhe GmbH, Karlsruhe, Fed. Rep. of Germany

[21] Appl. No.: 943,979

[22] Filed: Sep. 20, 1978

[30] Foreign Application Priority Data

Sep. 24, 1977 [DE] Fed. Rep. of Germany ....... 2743045

[51] Int. Cl.² ...................... C25B 15/08; C25B 11/03
[52] U.S. Cl. .................................. 204/272; 204/275; 204/284
[58] Field of Search ................ 204/233, 269, 272–273, 204/275, 284

[56] References Cited

U.S. PATENT DOCUMENTS

| | | | |
|---|---|---|---|
| 3,061,537 | 10/1962 | Yagishita | 204/275 |
| 3,728,245 | 4/1973 | Preis et al. | 204/275 |
| 3,770,612 | 11/1973 | Gray et al. | 204/273 X |
| 3,853,736 | 12/1974 | Harnden et al. | 204/269 |
| 3,869,374 | 3/1975 | Goldacker et al. | 204/269 X |

*Primary Examiner*—John H. Mack
*Assistant Examiner*—D. R. Valentine
*Attorney, Agent, or Firm*—Spencer & Kaye

[57] ABSTRACT

A counterflow extraction column for the liquid-liquid extraction of two phases during simultaneous electrolysis, includes an elongated, upright column tube containing a cathode and an anode. Within the tube, a common chamber defines cathodic zones and anodic zones and is void of separating members between the zones. The common chamber constitutes the anode chamber and the cathode chamber of the column.

5 Claims, 1 Drawing Figure

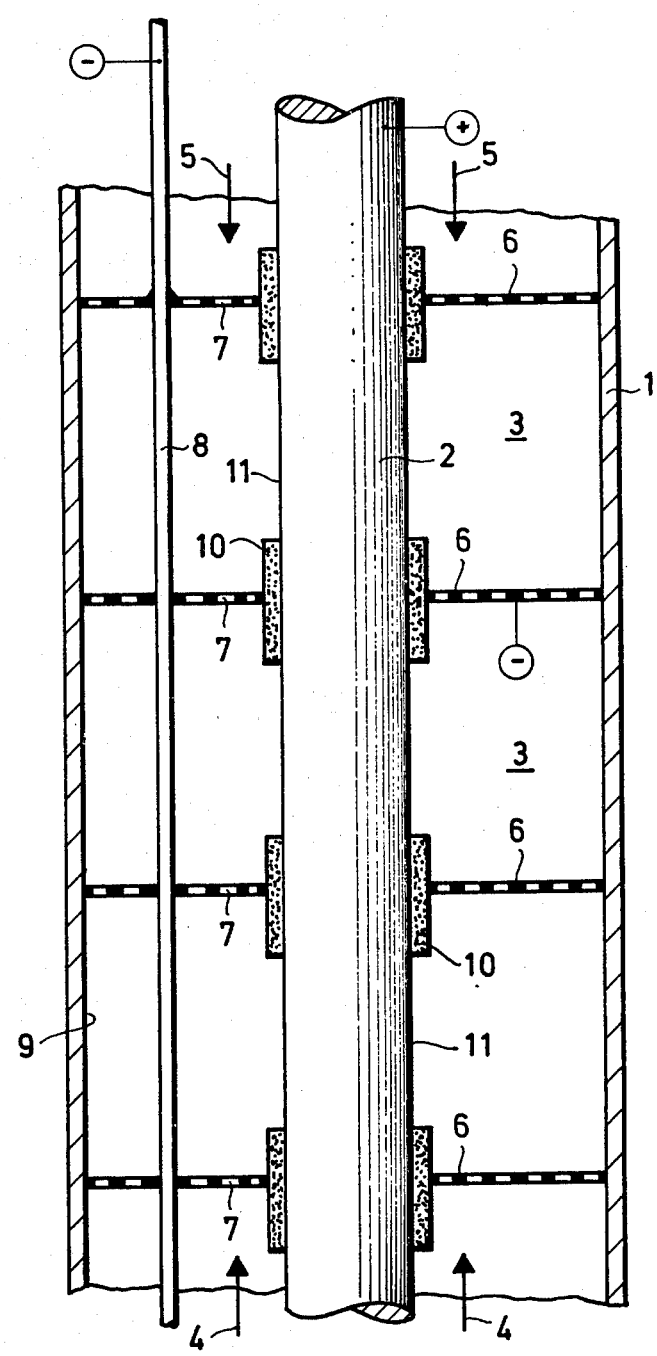

COUNTERFLOW EXTRACTION COLUMN

BACKGROUND OF THE INVENTION

This invention relates to a counterflow extraction column for the liquid-liquid extraction, during simultaneous electrolysis, of two phases which are insoluble in one another. The extraction column is preferably used for the separation of uranium-plutonium compounds and includes a vertically arranged, elongated tube in which there are arranged anodes, cathodes, as well as anode and cathode chambers which communicate with one another without diaphragms.

In a known column of the above-outlined type the anode chamber is separated from the cathode chamber by a tube containing nozzle plates, the apertures of which maintain communication between the two chambers. The nozzle plates constitute cross-sectional constrictions in the cathode chamber which may lead to a flooding of the column (phase reversal from a dispersed phase to a continuous phase) because of speed increase. In addition, after a longer service, in the tube or in the anode chamber an organic phase accumulates which has to be removed (drawn away) in a circumstantial manner. Further, such a removal adversely affects the reduction process.

It is a further disadvantage of the above-outlined known arrangements that the aqueous solutions can only be partially introduced into the reduction chamber (effective reaction), at best in a proportion that equals the ratio of the cross-sectional area of the annular extraction chamber to that of the cathode chamber. The separation effect of the cathode chamber with regard to the organic phase is thus not at an optimal value. This leads to a danger of stationary solvent accumulations in the central anode tube, as already mentioned above.

SUMMARY OF THE INVENTION

It is an object of the invention to provide an improved column of the above-outlined type from which the above-discussed disadvantages are eliminated by an integration of the electrolytically effective components in the column. In this manner, interference with the properties of extraction and results of separation predetermined by the system are substantially reduced.

This object and others to become apparent as the specification progresses, are accomplished by the invention, according to which, briefly stated, an undivided common chamber, having no separating elements, is used as the cathode and anode chamber for delimiting the cathode zones and anode zones.

According to a further advantageous feature of the invention, the anode is constituted by a central rod which projects through perforated plates functioning as cathodes and is electrically insulated therefrom.

According to a further feature of the invention, the cathodic perforated plates are constituted by simple, superposed apertured plate members which are connected to one another by means of an electric conductor and further, the cathodic perforated plates are directly affixed to the anode rod by means of insulating sleeves made, for example, of a ceramic material.

It is a further advantageous feature of the invention that the column tube (casing) may also function as a cathode and is, for this purpose, connected electrically with the perforated plates.

The particular advantage of the invention is to be regarded in the fact that the effective reaction (reduction) can occur directly in the extraction chamber, that is, the reduction and the extractive substance exchange are directly coupled with one another. The entire inner surface of the apparatus can serve as the cathode surface. If required, additional surfaces can be installed as cathodes or anodes without difficulty. Dead spaces in which stationary liquid quantities may accumulate are eliminated. Further, the structure of the column and its assembly is very simple. Also, mechanically stressed anode and cathode insulations, for example, central diaphragm tubes or central ceramic tubes (that had been fired to assume liquid impervious properties) as phase separators and platform carriers are also eliminated.

BRIEF DESCRIPTION OF THE DRAWING

The sole FIGURE illustrates a preferred embodiment of the invention in fragmentary longitudinal section.

DESCRIPTION OF THE PREFERRED EMBODIMENT

Turning now to the FIGURE, the counterflow extraction column illustrated therein comprises a vertically oriented elongated tube 1 made of a metal which resists the effect of the solution to be extracted and which, for example, may be high-grade steel, titanium or hafnium.

A rod 2 which functions as the anode extends coaxially within the tube 1; it may be platinum or a platinized carrier material. The annular chamber 3 defined between the rod 2 and the tube 1 serves as the extraction chamber in which the two phases 4 and 5 to be intermingled with one another are mixed and extracted while simultaneously an electrolysis is performed thereon. In the example illustrated, the phase 5 descending in the column 1 is an aqueous liquid (that is, an electrically conducting liquid), such as a nuclear fuel solution, while the ascending phase 4 is a non-conducting organic extraction medium, for example, tributyl phosphate.

The anode bar 2 carries uniformly spaced superimposed plates 6 which are provided with perforations 7. The extraction medium introduced into a pulsating manner repeatedly separates along the perforated plates 6 into droplet groups under the effect of the pulse amplitudes, so that a high speed of exchange is achieved.

The perforated plates 6, similarly to the tube 1, are made of a metal such as high-grade steel, titanium or hafnium and serve as the cathode. For this purpose, the plates 6 are electrically interconnected by means of a conductor 8. The latter serves as the cathode lead. Further, the perforated plates 6 may be electrically connected with the tube 1, so that both the surfaces of the perforated plates 6 and the inner face 9 of the tube 1 may function as the cathode.

Between the perforated plates 6 and the anode bar 2 which simultaneously serves as the anode lead, there are inserted ceramic sleeves 10 which, on the one hand, serve as a holding means for the perforated plates 6 and, on the other hand, function as an electric insulation between plate and bar. The effective upper face of the anode thus consists of the outer surfaces 11 of the anode bar 2 between the ceramic sleeves 10, while the effective cathode faces are the surfaces of the perforated plates 6 exposed to the liquid and the inner face 9 of the tube 1, in case the face 9 is electrically connected with the perforated plates 6. The chamber 3 thus defined constitutes the extraction chamber in which the electrolysis takes place and which, according to the invention, is no longer divided.

In the structure described above, the two electrodes, that is, the anode 2 and the cathode 6, 9 are arranged in or about the extraction chamber 3 without subdividing it further. Such a structure, which is a significant departure from earlier arrangements is feasible for the reason that it has been found that the organic phase at the anode as well as the anode surface when wetted by the organic phase is not appreciably damaged. Therefore, a subdivision of the chambers with interconnecting ports may be omitted.

In addition to the advantages discussed earlier, the column according to the invention has the further advantage that by means of the conversion of the discrete locations of reduction into continuous zones of reduction makes possible the use of lower current intensities. In this manner, the service life of the column is substantially increased, because of the decrease in the rate of corrosion. Further, in the column according to the invention, a phase reversion can no longer occur.

It is to be understood that the above description of the present invention is susceptible to various modifications, changes and adaptations, and the same are intended to be comprehended within the meaning and range of equivalents of the appended claims.

What is claimed is:

1. In a counterflow extraction column for the liquid-liquid extraction of two phases during simultaneous electrolysis; including an elongated, upright column tube containing a cathode and an anode; the improvement wherein said anode is a bar extending within said tube coaxially therewith and said cathode is formed of a plurality of spaced perforated plates centrally supported by the anode bar; the improvement further comprising means defining, within said tube, a common chamber defining cathodic zones and anodic zones and being void of separating members between said zones; said common chamber constituting an anode chamber and a cathode chamber; and insulating means for electrically insulating each said perforated plate from said anode bar.

2. A counterflow extraction column as defined in claim 1, wherein said perforated plates are sheet metal discs provided with a plurality of holes.

3. A counterflow extraction column as defined in claim 1, further comprising a conductor electrically connecting said perforated plates with one another.

4. A counterflow extraction column as defined in claim 1, wherein said insulating means includes an insulating sleeve passing through the center of the respective perforated plate and surrounding said anode bar, said insulating sleeve securing the respective perforated plate to said anode bar.

5. A counterflow extraction column as defined in claim 1, wherein said cathode is further formed by said tube; said tube being electrically connected to each said perforated plate.

* * * * *